United States Patent
Shin et al.

(10) Patent No.: US 10,626,507 B2
(45) Date of Patent: Apr. 21, 2020

(54) METHOD AND DEVICE FOR ELECTROCHEMICAL REDUCTION OF CARBON DIOXIDE

(71) Applicant: SOGANG UNIVERSITY RESEARCH FOUNDATION, Seoul (KR)

(72) Inventors: Woonsup Shin, Seoul (KR); Mi Jung Park, Seoul (KR)

(73) Assignee: Sogang University Research Foundation, Seoul (KR)

( * ) Notice: Subject to any disclaimer, the term of this patent is extended or adjusted under 35 U.S.C. 154(b) by 339 days.

(21) Appl. No.: 15/514,355

(22) PCT Filed: Sep. 30, 2015

(86) PCT No.: PCT/KR2015/010299
§ 371 (c)(1),
(2) Date: Jul. 24, 2017

(87) PCT Pub. No.: WO2016/052985
PCT Pub. Date: Apr. 7, 2016

(65) Prior Publication Data
US 2017/0350023 A1 Dec. 7, 2017

(30) Foreign Application Priority Data
Sep. 30, 2014 (KR) .................. 10-2014-0131254

(51) Int. Cl.
C25B 3/04 (2006.01)
C07C 51/41 (2006.01)
C25B 11/04 (2006.01)

(52) U.S. Cl.
CPC .............. *C25B 3/04* (2013.01); *C07C 51/41* (2013.01); *C25B 11/0405* (2013.01);
(Continued)

(58) Field of Classification Search
CPC ........................................................ C25B 3/04
(Continued)

(56) References Cited

U.S. PATENT DOCUMENTS

| 9,145,615 B2 | 9/2015 | Zhai et al. |
| 2013/0186771 A1 | 7/2013 | Zhai et al. |

(Continued)

FOREIGN PATENT DOCUMENTS

| CN | 101657568 A | 2/2010 |
| JP | 2013129883 A | 7/2013 |

(Continued)

OTHER PUBLICATIONS

Li et al., "The Electro-Reduction of Carbon Dioxide in a Continuous Reactor," Journal of Applied Electrochemistry (2005), vol. 35, pp. 955-965. (Year: 2005).*

(Continued)

*Primary Examiner* — Edna Wong
(74) *Attorney, Agent, or Firm* — Greer, Burns & Crain, Ltd.

(57) ABSTRACT

A method and a device for electrochemical reduction of carbon dioxide for preparing a high-concentration formate salt. Carbon dioxide is continuously supplied to a cathode unit and is continuously supplied to a metal hydroxide to the anode unit. A voltage or current is applied to the cathode unit and the anode unit for reducing the carbon dioxide to obtain the formate salt.

1 Claim, 19 Drawing Sheets

(52) U.S. Cl.
CPC ...... *C25B 11/0452* (2013.01); *C25B 11/0473* (2013.01); *C25B 11/0478* (2013.01)

(58) Field of Classification Search
USPC .................................................. 205/440, 457
See application file for complete search history.

(56) References Cited

U.S. PATENT DOCUMENTS

| | | | | |
|---|---|---|---|---|
| 2015/0047986 | A1* | 2/2015 | Shin | C25B 3/04 205/440 |
| 2016/0032470 | A1* | 2/2016 | Shin | C25B 11/18 205/440 |
| 2016/0298247 | A1* | 10/2016 | Shin | C25B 11/18 |

FOREIGN PATENT DOCUMENTS

| | | | |
|---|---|---|---|
| KR | 1020040009875 | 1/2004 | |
| KR | 1020080016198 | 2/2008 | |
| KR | 101324742 A | * 11/2013 | ............. C25B 11/18 |
| KR | 101324742 B1 | 11/2013 | |
| KR | 102014000323 A | * 1/2014 | ............... C25B 3/04 |
| KR | 1020140003233 | 1/2014 | |
| KR | 101372532 | 3/2014 | |
| KR | 1020140073007 | 6/2014 | |
| WO | 2012040503 | 3/2012 | |

OTHER PUBLICATIONS

Cao et al., "Electrocatalytic Reduction of Carbon Dioxide Using Cobalt Tetrakis(4-trimethylammoniophenyl)porphyrin Iodide Under High Pressure," Huaxue Xuebao (1986), vol. 44, No. 3, pp. 220-224. Abstract Only. (Year: 1986).*
International Search Report, dated Jan. 7, 2016 for Appl. No. PCT/KR2015/010299.

* cited by examiner

METHOD AND DEVICE FOR ELECTROCHEMICAL REDUCTION OF CARBON DIOXIDE

This application is a U.S. national phase of International Application No. PCT/KR2015/010299 filed on Sep. 30, 2015, which claims priority to KR 10-2014-0131254 filed on Sep. 30, 2014, the entirety of both of which are hereby incorporated by reference.

TECHNICAL FIELD

The invention relates to a method for electrochemical reduction of carbon dioxide to prepare a high-concentration formate salt, and a device for electrochemical reduction of carbon dioxide to prepare the high-concentration formate salt.

BACKGROUND

Carbon-based materials on the earth are maintained at a constant amount and balanced while forming carbon cycles in various forms. However, due to the increase in atmospheric carbon dioxide ($CO_2$) which is one of the materials forming carbon cycles, such a balance is being broken. According to the National Oceanic and Atmospheric Administration (NOAA)'s report of trend in atmospheric $CO_2$, the concentration of atmospheric $CO_2$ before industrialization remained at about 280 ppm (parts per million), but has geometrically increased after industrialization and exceeded about 350 ppm in 1989 and then has steadily increased and exceeded the maximum limit, i.e., about 400 ppm, in May 2012 and remained at a monthly average of about 400 ppm as of April 2014.

The increase in concentration of atmospheric $CO_2$ has been caused by the increase in $CO_2$ emissions after industrialization, and the $CO_2$ emissions have continuously increased since the first measurement in 1965 (about 12 billion tons), and as of 2012, more than about 34 billion tons of $CO_2$ has been emitted a year. In the current system largely depending on fossil fuels as energy, the increase in $CO_2$ emissions is expected to continue.

The $CO_2$ emissions are problems not only for other countries. Korea has also much contributed to $CO_2$ emissions, and according to the result of analyzing the report [LONG-TERM TREND IN GLOBAL $CO_2$ EMISSIONS] prepared by the Joint Research Centre (JRC) and the Netherlands Environment Assessment Agency (PBL), the $CO_2$ emissions in Korea have also increased by about 136% in the last 20 years and the rate of increase is the third highest in the world, following China (about 256%) and India (about 179%). Further, the $CO_2$ emissions in Korea was ranked ninth in the world in 2008 and rose to eighth place in 2009 and also rose to seventh place in the world in 2010 and have remained in that place ever since.

The biggest problem caused by the increase in atmospheric $CO_2$ is global warming. The Intergovernmental Panel on Climate Change (IPCC) diagnosed that all the countries of the world have been unwilling to deal with climate change and if $CO_2$ emissions cannot be suppressed in the next 15 years, the climate change problem would be worsened to a level which cannot be actually solved by current technology. As such, with awareness of the danger of the rapid increase in atmospheric $CO_2$, studies for removing atmospheric $CO_2$ are being actively conducted around the world.

As a technology for removing atmospheric $CO_2$, Carbon Capture and Storage (CCS) has been actively studied till recently. However, CCS needs a wide space to store captured $CO_2$ and also has a risk caused by the storage of a large amount of $CO_2$ in one place. Due to this problem, Carbon Capture and Utilization (CCU) technology capable of directly converting captured $CO_2$ into useful materials without storage has received a lot of attention in recent years. The CCS is a technology of burying and discarding the captured $CO_2$ as waste resource, whereas the CCU is a technology of recycling the captured $CO_2$ into a high-value product. Since $CO_2$ is the most abundant carbon source on the earth, various technologies for converting $CO_2$ into useful materials are being studied.

Currently, recycling of $CO_2$ is being studied mainly in the fields of converting $CO_2$ into useful chemicals such as acetate, polycarbonate, and the like through a catalytic method [Korean Patent Laid-open Publication No. 10-2008-0016198], producing bio fuels using living organisms such as microalgae, producing renewable fuels such as methanol using water and $CO_2$ through artificial photosynthesis, and producing construction materials such as cement by reacting $CO_2$ with calcium salt or magnesium salt to be converted into minerals according to a natural rock formation process occurring in clams or oysters. As such, recycling of $CO_2$ is being studied in various fields.

As a technology for converting $CO_2$ into useful materials, an electrochemical conversion method is also being studied. The electrochemical conversion of $CO_2$ is a kind of catalytic method and uses electric energy to convert $CO_2$ through an electrode reaction, and can convert $CO_2$ at relatively room temperature and atmospheric pressure, uses a simple device, and can also selectively produce a product depending on the kind of a working electrode used in the system, and, thus, it is an effective method of converting $CO_2$.

DISCLOSURE OF THE INVENTION

Problems to be Solved by the Invention

The present disclosure provides a method for electrochemical reduction of carbon dioxide to prepare a high-concentration formate salt and a device for electrochemical reduction of carbon dioxide to prepare the high-concentration formate salt.

However, problems to be solved by the present disclosure are not limited to the above-described problems, and although not described herein, other problems to be solved by the present disclosure can be clearly understood by those skilled in the art from the following descriptions.

Means for Solving the Problems

In accordance with a first aspect of the present disclosure, there is provided a method for electrochemical reduction of carbon dioxide, including: in a reactor of electrochemical reduction of carbon dioxide including an anode unit and a cathode unit, supplying carbon dioxide to the cathode unit, continuously supplying a metal hydroxide to the anode unit, and applying voltage or current to the cathode unit and the anode unit for reducing the carbon dioxide to obtain a formate salt.

In accordance with a second aspect of the present disclosure, there is provided a device for electrochemical reduction of carbon dioxide, including: an anode unit separated from a cathode unit by a membrane; a first chamber including a cathode solution to be supplied to the cathode unit; a second chamber including an anode solution containing a metal hydroxide to be supplied to the anode unit; and a supply unit configured to apply voltage or current to the cathode unit and the anode unit, and the metal hydroxide is continuously supplied to the anode unit, carbon dioxide gas is continuously supplied into the cathode solution, and voltage or current is applied to the cathode unit and the anode unit for reducing the carbon dioxide to obtain a formate salt.

Effects of the Invention

According to an exemplary embodiment of the present disclosure, when formate (HCOOH) is generated through an electrochemical method of carbon dioxide, a two-electron reaction occurs, so that preparing the formate consumes less energy than preparing other products generated through an electrochemical method of carbon dioxide, and the formate is expensive and thus highly profitable in comparison with energy consumption. Also, the formate is a liquid product and thus easy to store and transport.

Further, during electrochemical reduction of carbon dioxide, metal hydroxide is continuously added to the anode unit, so that a pH and voltage of an electrolyte included in the anode unit can be maintained uniformly to maintain a balance between the anode unit and the cathode unit, and positive ions such as $K^+$, $Na^+$, or $Li^+$ are continuously supplied, so that a formate salt having a high concentration of about 0.5 M or more can be continuously obtained for a long time.

BEST MODE FOR CARRYING OUT THE INVENTION

Figure 1:
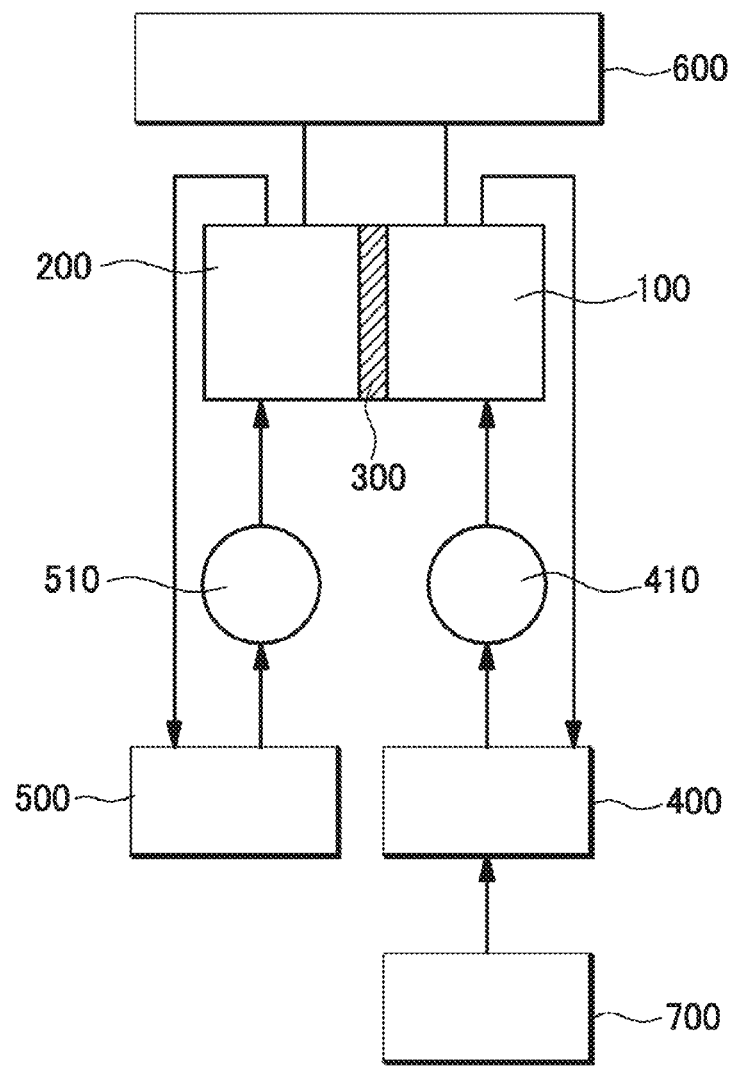
FIG. 1 is a schematic view illustrating a device for electrochemical reduction of carbon dioxide in accordance with an exemplary embodiment of the present disclosure.

Hereinafter, examples of the present disclosure will be described in detail with reference to the accompanying drawings so that the present disclosure may be readily implemented by those skilled in the art. However, it is to be noted that the present disclosure is not limited to the examples but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element.

Through the whole document, the term "on" that is used to designate a position of one element with respect to another element includes both a case that the one element is adjacent to the another element and a case that any other element exists between these two elements.

Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise. Through the whole document, the term "about or approximately" or "substantially" are intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document, the term "combination(s) of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document, a phrase in the form "A and/or B" means "A or B, or A and B".

Hereinafter, exemplary embodiments and examples of the present disclosure will be described in detail with reference to the accompanying drawings, but the present disclosure may not be limited to the following exemplary embodiments and examples.

In accordance with a first aspect of the present disclosure, there is provided a method for electrochemical reduction of carbon dioxide, including: in a reactor of electrochemical reduction of carbon dioxide including an anode unit and a cathode unit, supplying carbon dioxide to the cathode unit, continuously supplying a metal hydroxide to the anode unit, and applying voltage or current to the cathode unit and the anode unit for reducing the carbon dioxide to obtain a formate salt.

In an exemplary embodiment of the present disclosure, an electrolyte included in the cathode solution and the anode solution may include a member selected from the group consisting of $K_2SO_4$, $KHCO_3$, $KCl$, $KOH$, and combinations thereof, but may not be limited thereto. In an exemplary embodiment of the present disclosure, if $KHCO_3$ is used as the electrolyte, $KCl$ may be used together as a subsidiary electrolyte in order to improve the conductivity, but the present disclosure may not be limited thereto. For example, if $KHCO_3$ and $KCl$ are used as the electrolyte, carbon dioxide can be converted for a long time with a stable current efficiency, but if electrolysis is performed for a long time, $Cl^-$ ions may be transferred to the anode unit, so that chlorine ($Cl_2$) may be generated. The chlorine may cause corrosion of metal or melting of a tube. In an exemplary embodiment of the present disclosure, if only $KHCO_3$ is used as the electrolyte, the conductivity is decreased, so that the efficiency may be decreased by about 10%. In an exemplary embodiment of the present disclosure, if $K_2SO_4$ is used as the electrolyte, the efficiency is increased by from about 5% to about 10% as compared with the case where $KHO_3$ and $KCl$ are used as the electrolyte, and chlorine is not generated, so that problems such as corrosion can be solved. However, if $K_2SO_4$ is used as the electrolyte included in the cathode solution to obtain more than about 0.5 M formate salt, the $K_2SO_4$ may be deposited. Thus, $K_2SO_4$ may be deposited within a glass-frit for supplying a $CO_2$ gas, so that $CO_2$ may not be supplied properly or a solution may not circulate due to crystals. In an exemplary embodiment of the present disclosure, less than 0.5 M $K_2SO_4$ may be used, so that deposition of the $K_2SO_4$ can be solved, but the present disclosure may not be limited thereto.

In accordance with an exemplary embodiment of the present disclosure, the metal hydroxide may include an alkali metal hydroxide, but may not be limited thereto.

In accordance with an exemplary embodiment of the present disclosure, the metal hydroxide may include a member selected from the group consisting of KOH, NaOH, LiOH, and combinations thereof, but may not be limited thereto.

In accordance with an exemplary embodiment of the present disclosure, the metal hydroxide is continuously supplied to the anode unit so that formate salt with a high concentration of about 0.5 M or more can be continuously obtained by reduction of the carbon dioxide, but may not be limited thereto. For example, the formate salt obtained according to an exemplary embodiment of the present disclosure may have a high concentration of about 0.5 M or more, about 0.8 M or more, about 1 M or more, about 1.3 M or more, about 1.5 M or more, about 1.8 M or more, about 2 M or more, about 2.3 M or more, about 2.5 M or more, about 2.8 M or more, or about 3 M or more, but may not be limited thereto.

In an exemplary embodiment of the present disclosure, if a predetermined concentration or more of formate salt is generated during long term electrolysis, voltage may be rapidly changed, which may cause a rapid change in pH of the anode solution. The rapid change in pH is caused by the collapse of a buffer system of the cathode solution occurring when hydrogen ions generated in the anode solution are oversupplied to the cathode solution through a membrane. Therefore, if the metal hydroxide is continuously supplied into the anode solution, the generated hydrogen ions are neutralized, so that a pH and voltage of the anode solution can be maintained uniformly, and, thus, the amount of oversupplied hydrogen ions can be adjusted and electrolysis can be performed for a long time. Further, since the metal hydroxide is continuously supplied, positive metal ions of the metal hydroxide are also continuously supplied. Therefore, the formate salt with a high concentration of about 0.5 M or more can be continuously obtained for a long time.

In accordance with an exemplary embodiment of the present disclosure, a current density depending on the voltage applied to the cathode unit and the anode unit may be about 350 $mA/cm^2$ or less, but may not be limited thereto. For example, the current density may be from about 2 $mA/cm^2$ to about 350 $mA/cm^2$, from about 2 $mA/cm^2$ to about 300 $mA/cm^2$, from about 2 $mA/cm^2$ to about 250 $mA/cm^2$, from about 2 $mA/cm^2$ to about 200 $mA/cm^2$, from about 2 $mA/cm^2$ to about 150 $mA/cm^2$, from about 2 $mA/cm^2$ to about 100 $mA/cm^2$, from about 2 $mA/cm^2$ to about 50 $mA/cm^2$, from about 2 $mA/cm^2$ to about 10 $mA/cm^2$, from about 10 $mA/cm^2$ to about 350 $mA/cm^2$, from about 50 $mA/cm^2$ to about 350 $mA/cm^2$, from about 100 $mA/cm^2$ to about 350 $mA/cm^2$, from about 150 $mA/cm^2$ to about 350 $mA/cm^2$, from about 200 $mA/cm^2$ to about 350 $mA/cm^2$, from about 250 $mA/cm^2$ to about 350 $mA/cm^2$, or from about 300 $mA/cm^2$ to about 350 $mA/cm^2$, but may not be limited thereto.

In accordance with an exemplary embodiment of the present disclosure, the cathode unit may include tin, mercury, lead, indium, or an amalgam electrode, but may not be limited thereto.

In accordance with an exemplary embodiment of the present disclosure, the amalgam electrode may include a metal formed (loaded) on a surface of a substrate electrode, and the metal includes a member selected from the group consisting of Hg, Ag, In, Sn, Pb, Cu, and combinations thereof, but may not be limited thereto.

In an exemplary embodiment of the present disclosure, the amalgam electrode may include dental amalgam, but may not be limited thereto. The dental amalgam may supply a safe amalgam electrode with negligible toxicity of mercury.

In an exemplary embodiment of the present disclosure, the amalgam electrode may include Hg in the amount of from about 35 parts by weight to about 55 parts by weight, Ag in the amount of from about 14 parts by weight to about 34 parts by weight, Sn in the amount of from about 7 parts by weight to about 17 parts by weight, and Cu in the amount of from about 4 parts by weight to about 24 parts by weight, but may not be limited thereto.

In accordance with an exemplary embodiment of the present disclosure, the substrate electrode may include a porous substrate, a plate-type substrate, a rod-type substrate, or a foam-type substrate, but may not be limited thereto. For example, the substrate electrode having porosity may include a granular aggregate, a surface-treated porous electrode, a mesh-type metal electrode, but may not be limited thereto.

In an exemplary embodiment of the present disclosure, the substrate electrode may include a member selected from the group consisting of copper, tin, nickel, carbon, glassy carbon, silver, gold, and combinations thereof, but may not be limited thereto.

In an exemplary embodiment of the present disclosure, the amalgam electrode may be formed by using an amalgamator or by electroplating, but may not be limited thereto.

In accordance with a second aspect of the present disclosure, there is provided a device for electrochemical reduction of carbon dioxide, including: an anode unit separated from a cathode unit by a membrane; a first chamber including a cathode solution to be supplied to the cathode unit; a second chamber including an anode solution containing a metal hydroxide to be supplied to the anode unit; and a supply unit configured to apply voltage or current to the cathode unit and the anode unit, and the metal hydroxide is continuously supplied to the anode unit, carbon dioxide gas is continuously supplied into the cathode solution, and voltage or current is applied to the cathode unit and the anode unit for reducing the carbon dioxide to obtain a formate salt.

Since the second aspect of the present disclosure relates to a device for electrochemical reduction of carbon dioxide in accordance with the first aspect of the present disclosure, detailed descriptions of the device for electrochemical reduction of carbon dioxide, which overlap with those of the first aspect of the present disclosure, are omitted hereinafter, but the descriptions of the first aspect of the present disclosure may be identically applied to the second aspect of the present disclosure, even though they are omitted hereinafter.

In this regard, FIG. 1 is a schematic view illustrating a device for electrochemical reduction of carbon dioxide in accordance with an exemplary embodiment of the present disclosure. The device for electrochemical reduction of carbon dioxide in accordance with an exemplary embodiment of the present disclosure includes a cathode unit 100, an anode unit 200, a membrane 300 configured to separate the cathode unit 100 and the anode unit 200, a first chamber 400 connected to the cathode unit 100 and configured to supply a cathode solution to the cathode unit 100, a second chamber 500 connected to the anode unit 200 and configured to supply an anode solution to the anode unit 200, a carbon dioxide supply unit 700 connected to the first chamber 400 and configured to supply carbon dioxide to the cathode unit 100, and a supply unit 600 connected to each of the cathode unit 100 and the anode unit 200 and configured to apply voltage or current to the cathode unit 100 and the anode unit 200.

In an exemplary embodiment of the present disclosure, the supply unit 600 may include a constant voltage circuit or a constant current circuit, but may not be limited thereto.

In an exemplary embodiment of the present disclosure, the device may further include a first pump 410 connected to the first chamber 400 and a second pump 510 connected to the second chamber 500, but may not be limited thereto. The cathode solution and the anode solution may be circulated by the first pump 410 and the second pump 510, but may not be limited thereto.

Figure 2:
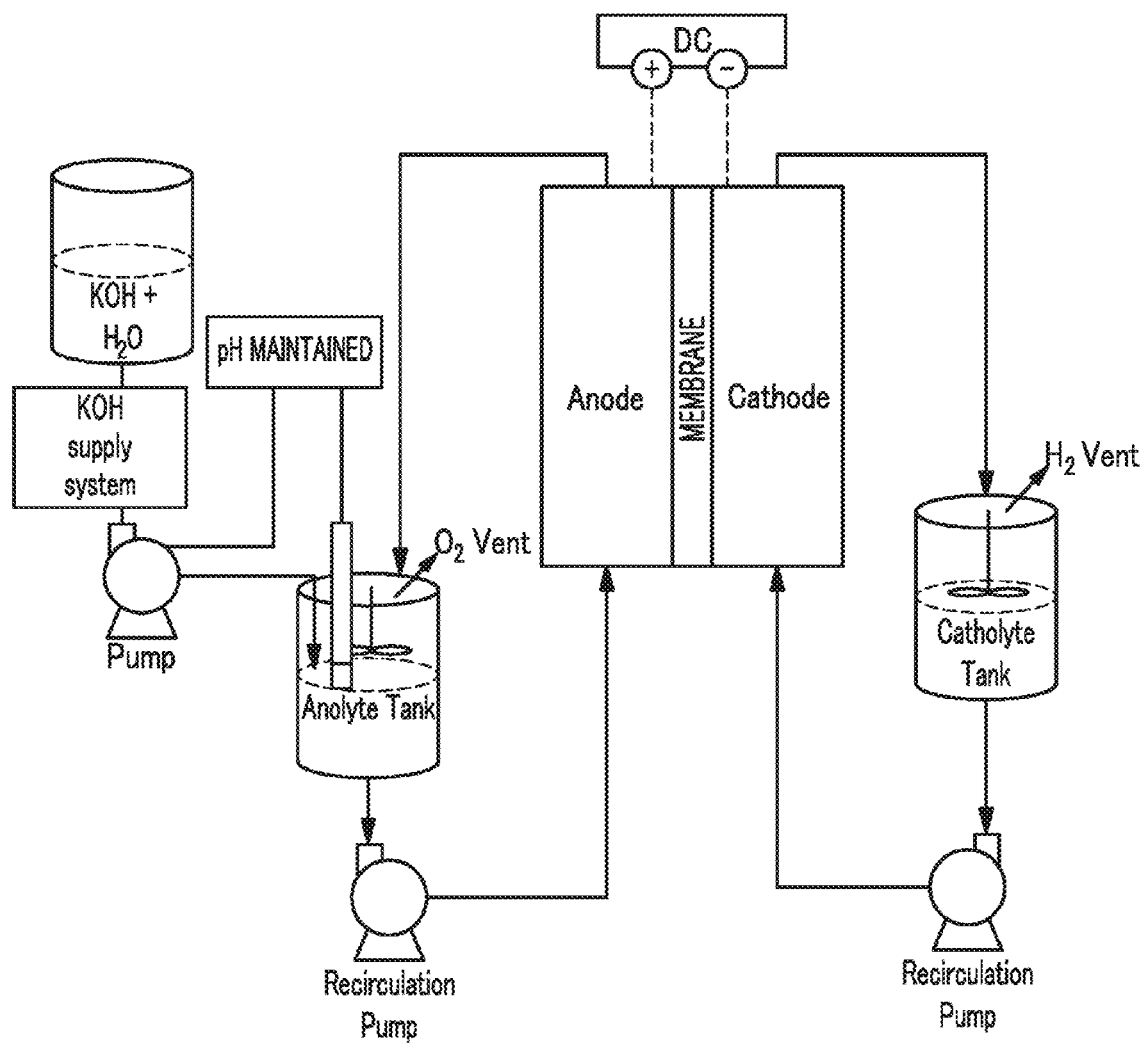
FIG. 2 is a schematic view illustrating a device for electrochemical reduction of carbon dioxide in accordance with an exemplary embodiment of the present disclosure.

In an exemplary embodiment of the present disclosure, more desirably, the device for electrochemical reduction of carbon dioxide illustrated in FIG. 1 may have the same configuration as illustrated in FIG. 2, but may not be limited thereto.

In an exemplary embodiment of the present disclosure, the device may further include a metal hydroxide supply system connected to the second chamber, but may not be limited thereto. For example, the supply of the metal hydroxide to the second chamber may be the supply of a metal hydroxide solution to the second chamber (anolyte tank) by circulating a mixed solution of the metal hydroxide and water by a pump as illustrated in FIG. 2, but may not be limited thereto.

In accordance with an exemplary embodiment of the present disclosure, the metal hydroxide may include an alkali metal hydroxide, but may not be limited thereto.

In accordance with an exemplary embodiment of the present disclosure, the metal hydroxide may include a member selected from the group consisting of KOH, NaOH, LiOH, and combinations thereof, but may not be limited thereto.

In accordance with an exemplary embodiment of the present disclosure, a current density depending on the voltage applied to the cathode unit and the anode unit may be about 350 mA/cm$^2$ or less, but may not be limited thereto.

In accordance with an exemplary embodiment of the present disclosure, the metal hydroxide is continuously supplied to the anode unit so that a formate salt with a high concentration of about 0.5 M or more can be continuously obtained by reduction of the carbon dioxide, but may not be limited thereto.

In accordance with an exemplary embodiment of the present disclosure, the cathode unit may include tin, mercury, lead, indium, or an amalgam electrode, but may not be limited thereto.

In accordance with an exemplary embodiment of the present disclosure, the amalgam electrode may include a metal formed (loaded) on a surface of a substrate electrode, and the metal includes a member selected from the group consisting of Hg, Ag, In, Sn, Pb, Cu, and combinations thereof, but may not be limited thereto.

In an exemplary embodiment of the present disclosure, the amalgam electrode may include dental amalgam, but may not be limited thereto. The dental amalgam may supply a safe amalgam electrode with negligible toxicity of mercury.

In an exemplary embodiment of the present disclosure, the amalgam electrode may include Hg in the amount of from about 35 parts by weight to about 55 parts by weight, Ag in the amount of from about 14 parts by weight to about 34 parts by weight, Sn in the amount of from about 7 parts by weight to about 17 parts by weight, and Cu in the amount of from about 4 parts by weight to about 24 parts by weight, but may not be limited thereto.

In accordance with an exemplary embodiment of the present disclosure, the substrate electrode may include a porous substrate, a plate-type substrate, a rod-type substrate, or a foam-type substrate, but may not be limited thereto.

MODE FOR CARRYING OUT THE INVENTION

Hereinafter, Examples of the present disclosure will be described in more detail. However, the present disclosure may not be limited thereto.

EXAMPLE

Figure 3:
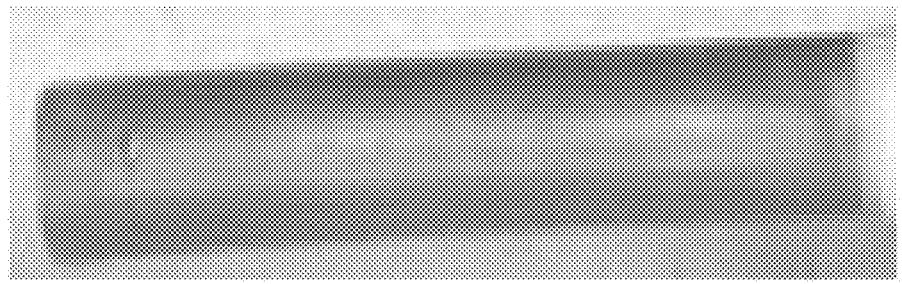
FIG. 3 shows a rod-type electrode in accordance with an example of the present disclosure.
Figure 4:
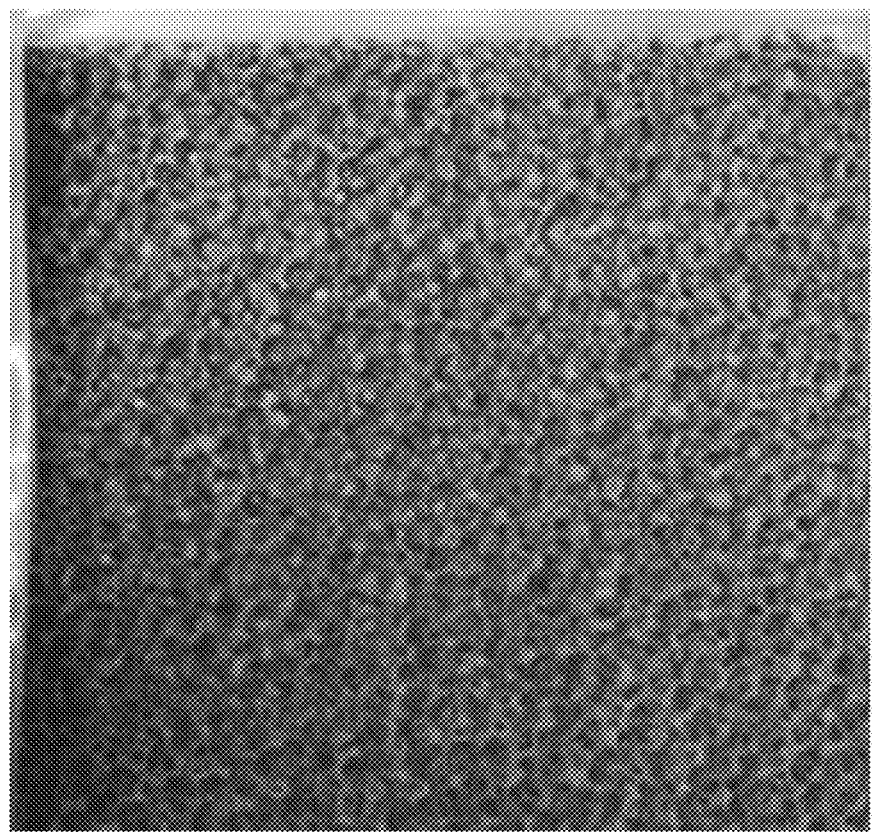
FIG. 4 shows a foam-type electrode in accordance with an example of the present disclosure.
Figure 5:
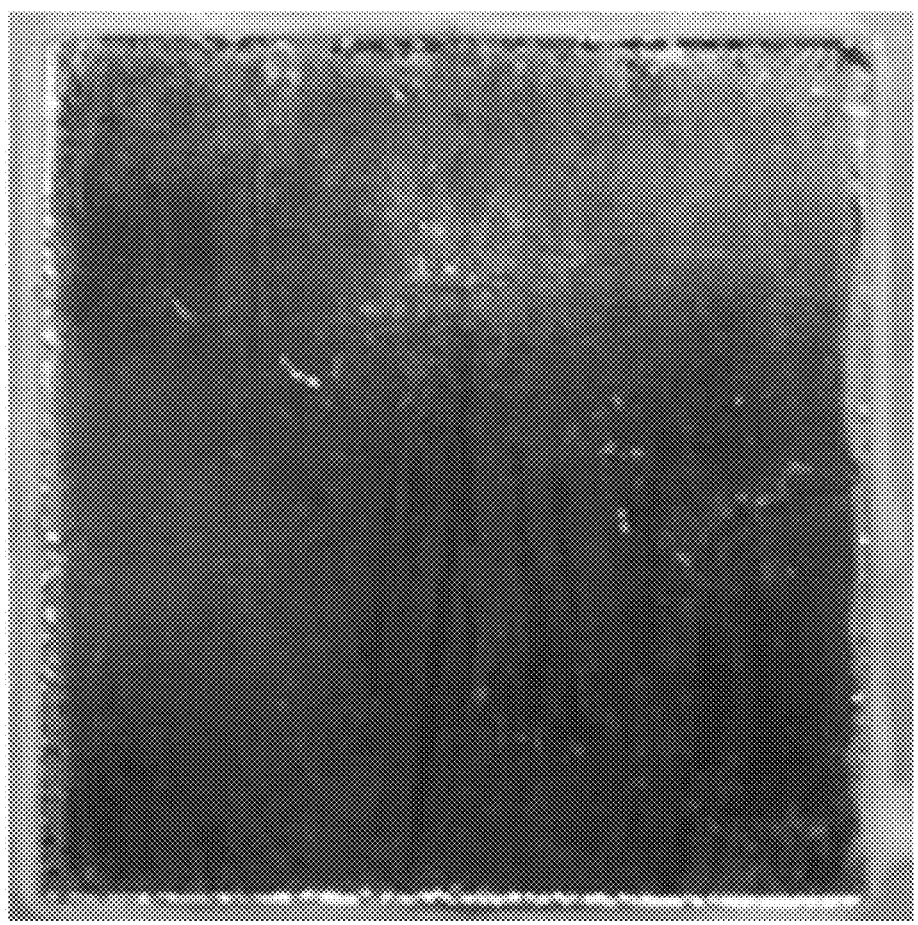
FIG. 5 shows a plate-type electrode in accordance with an example of the present disclosure.
Figure 6:
FIG. 6 shows a flow cell system for electrochemical $CO_2$ conversion in accordance with an example of the present disclosure.

Generation of a High-Concentration Formate Salt Using the Method and Device for Electrochemical Reduction of Carbon Dioxide A test for electrochemical conversion of carbon dioxide using a flow cell was performed in order to produce high-concentration formate. An amalgam-coated rod-type electrode (FIG. 3), an amalgam-coated foam-type electrode (FIG. 4), or an amalgam-coated plate-type electrode (FIG. 5) were used as a working electrode and an IrOx-coated titanium mesh DSA electrode was used as a counter electrode, and a constant current was applied and then, voltages were measured from both ends. A cathode solution was supplied to a cathode unit and an anode solution was supplied to an anode unit, and the carbon dioxide conversion system used herein is as shown in FIG. 6.

Figure 7:
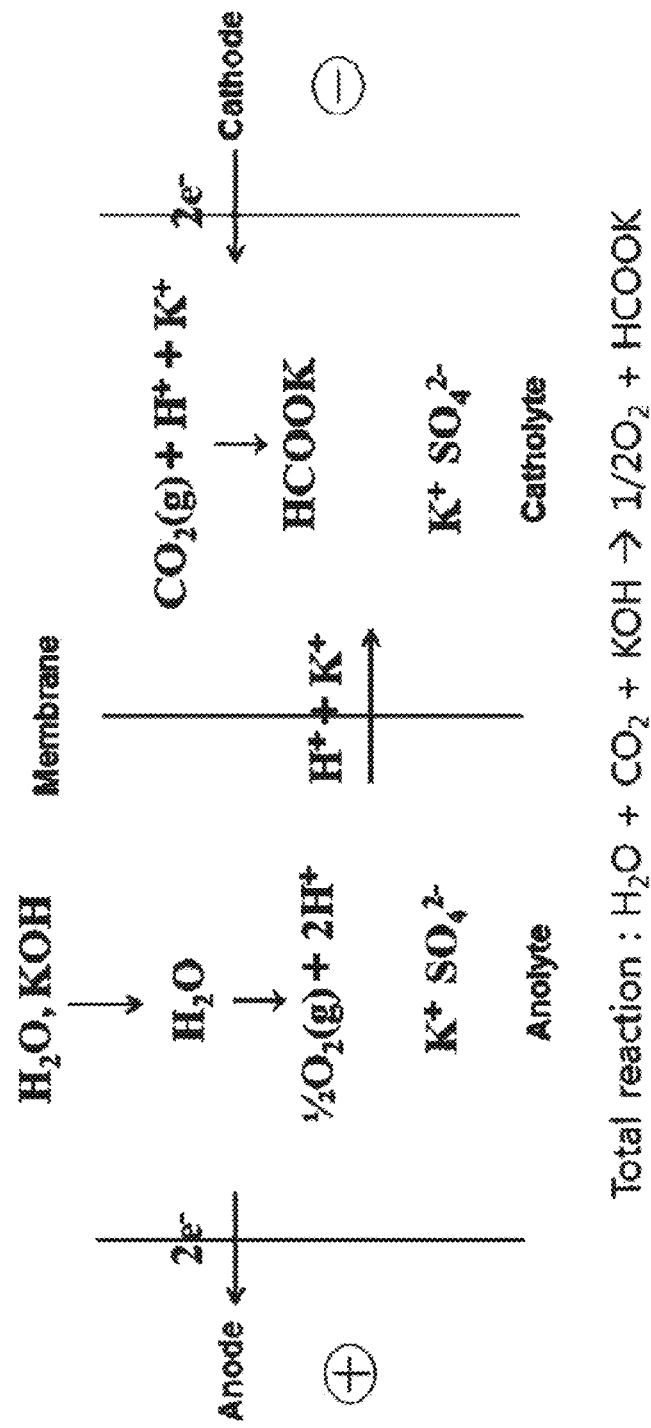
FIG. 7 shows a mass balance in a $K_2SO_4$ system during $CO_2$ conversion in accordance with an example of the present disclosure.
Figure 8:
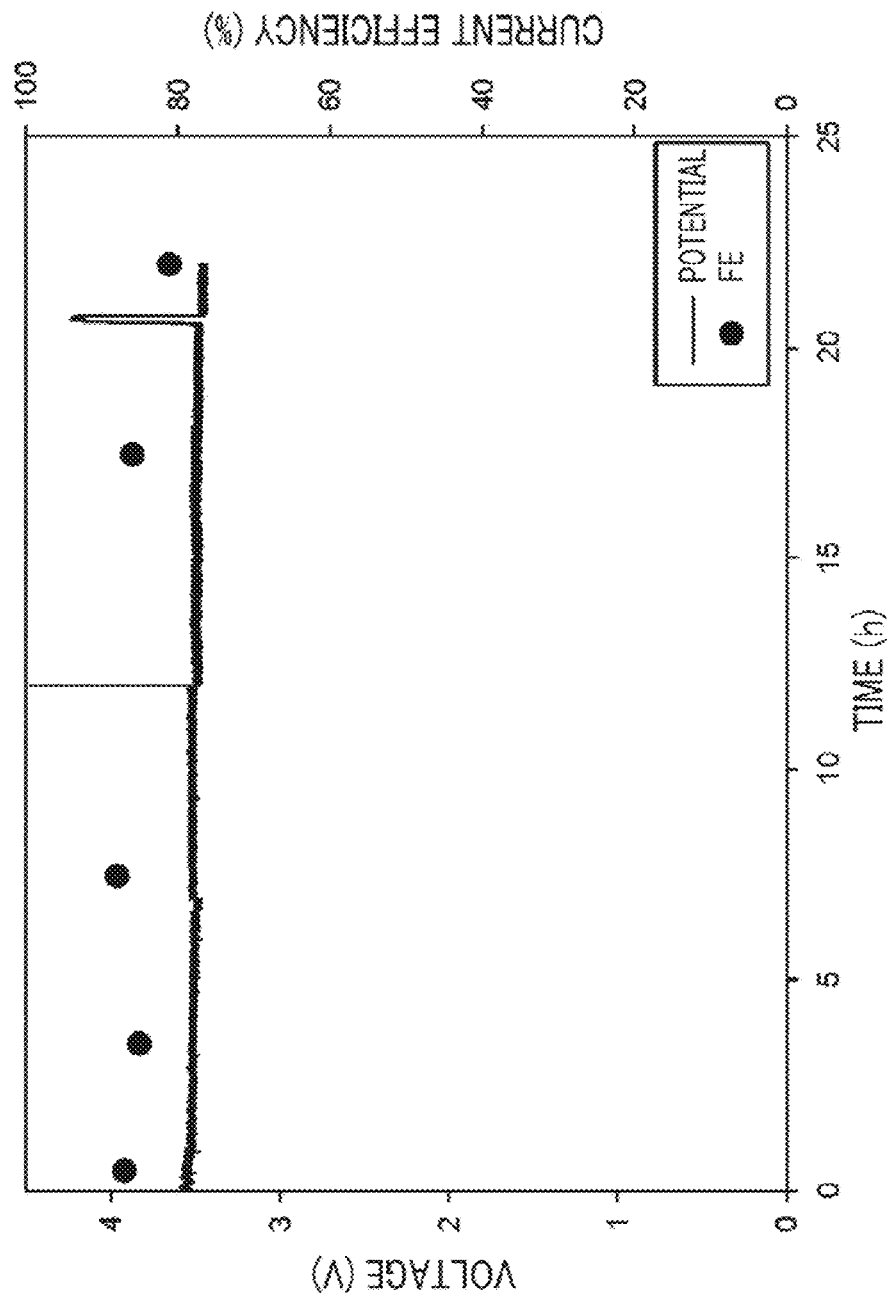
FIG. 8 shows electrolysis of $CO_2$ by an amalgam-coated foam-type copper electrode in a flow-cell including 0.5 M $K_2SO_4$ in accordance with an example of the present disclosure.
Figure 9:
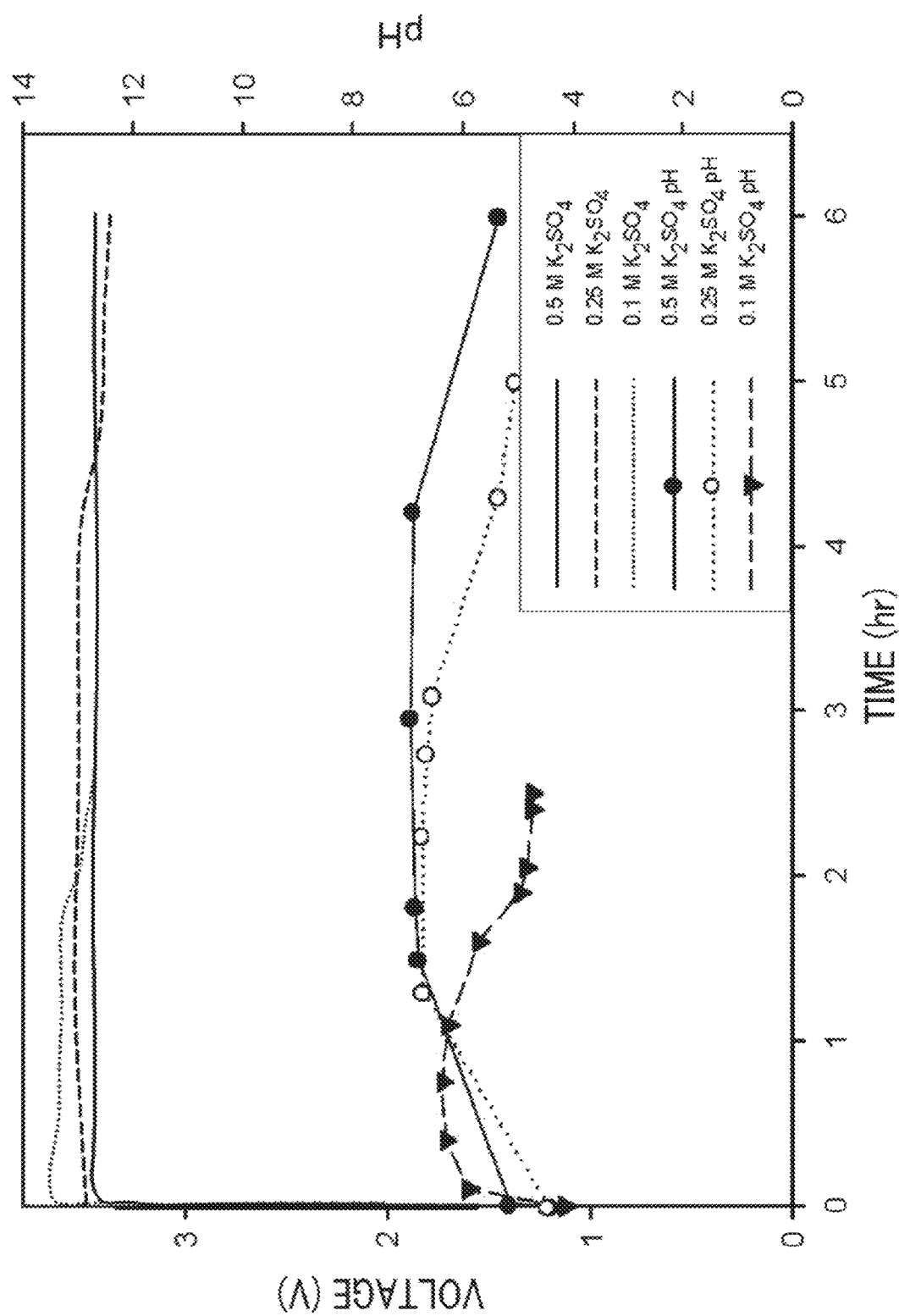
FIG. 9 is a graph showing an effect of an electrolyte concentration on flow-cells respectively including 0.1 M, 0.25 M, and 0.5 M $K_2SO_4$ in accordance with an example of the present disclosure.

In general, a pH of an anode unit and a cathode unit is continuously changed during electrolysis for a long time, so that the efficiency is decreased. In order to solve this problem, in the present Example, it was observed that when a 5 M potassium hydroxide (KOH) solution was continuously added to the anode unit to uniformly maintain a pH of an electrolyte in the anode unit, a pH of the cathode unit was also uniformly maintained and on this occasion, FIG. 7 shows ion balance in an electrolyte within the carbon dioxide conversion system using potassium sulfate as the electrolyte. As a result of the test using potassium sulfate as the electrolyte, the efficiency was from 80% to 90% (FIG. 8). It was observed that when $K_2SO_4$ with a too low concentration was used, an ion concentration was low, so that the conductivity was relatively decreased, resulting in an increase in cell voltage and a decrease in efficiency, and a concentration of K+ ions in the solution was low, so that when all of the ions were consumed, a pH and voltage were rapidly changed (FIG. 9).

A potentiostat (EG&G, 273A) and a constant current circuit (KS RnD, $CO_2$ 10A) were used to perform electrolysis. In this case, a foam-type electrode (3 cm×3 cm, 0.5 cm thick) was used as a working electrode and an electrolyte volume was used in a various range of from 100 mL to 1,000 mL and mainly in the range of from 100 mL to 200 mL. An electrolyte of the anode unit and an electrolyte of the cathode unit were separated by a Nafion 117 membrane before use. Ultra-pure carbon dioxide (with a purity of 99.99%) was continuously supplied to the electrolyte of the cathode unit using a glass-frit and ultra-pure argon (with a purity of 99.99%) was continuously supplied to the electrolyte of the anode unit or electrolysis was performed thereto without injecting a gas. A diaphragm pump and a peristaltic pump were used as pumps for circulating a solution. Formate salt as a product was quantitatively analyzed by liquid chromatography.

Test Example 1

Increase in Current Density Using Electrode

Figure 10:
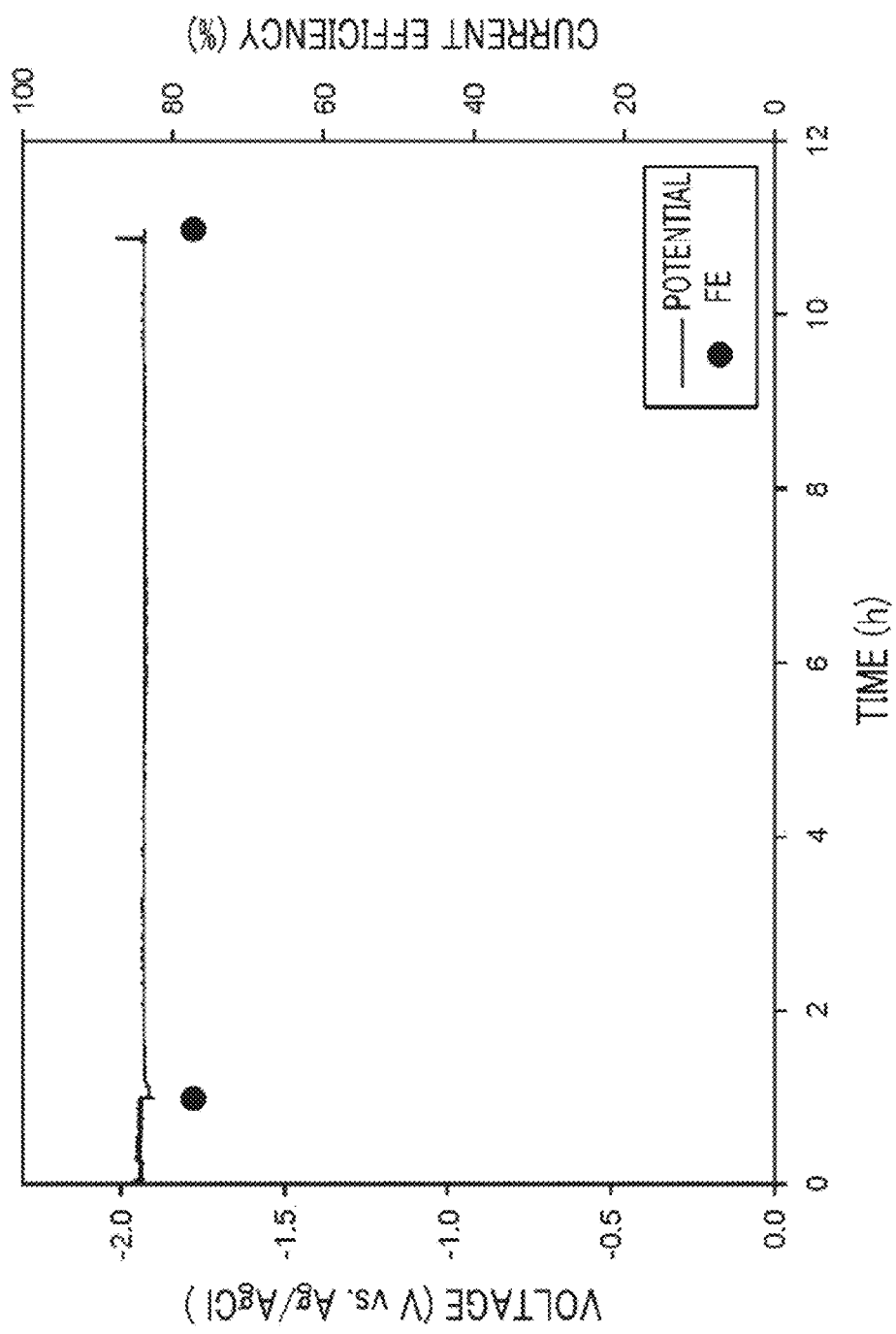
FIG. 10 shows electrolysis of $CO_2$ by an amalgam-coated rod-type electrode in a H-type cell including 0.5 M $KHCO_3$ and 2 M KCl in accordance with an example of the present disclosure.
Figure 11:
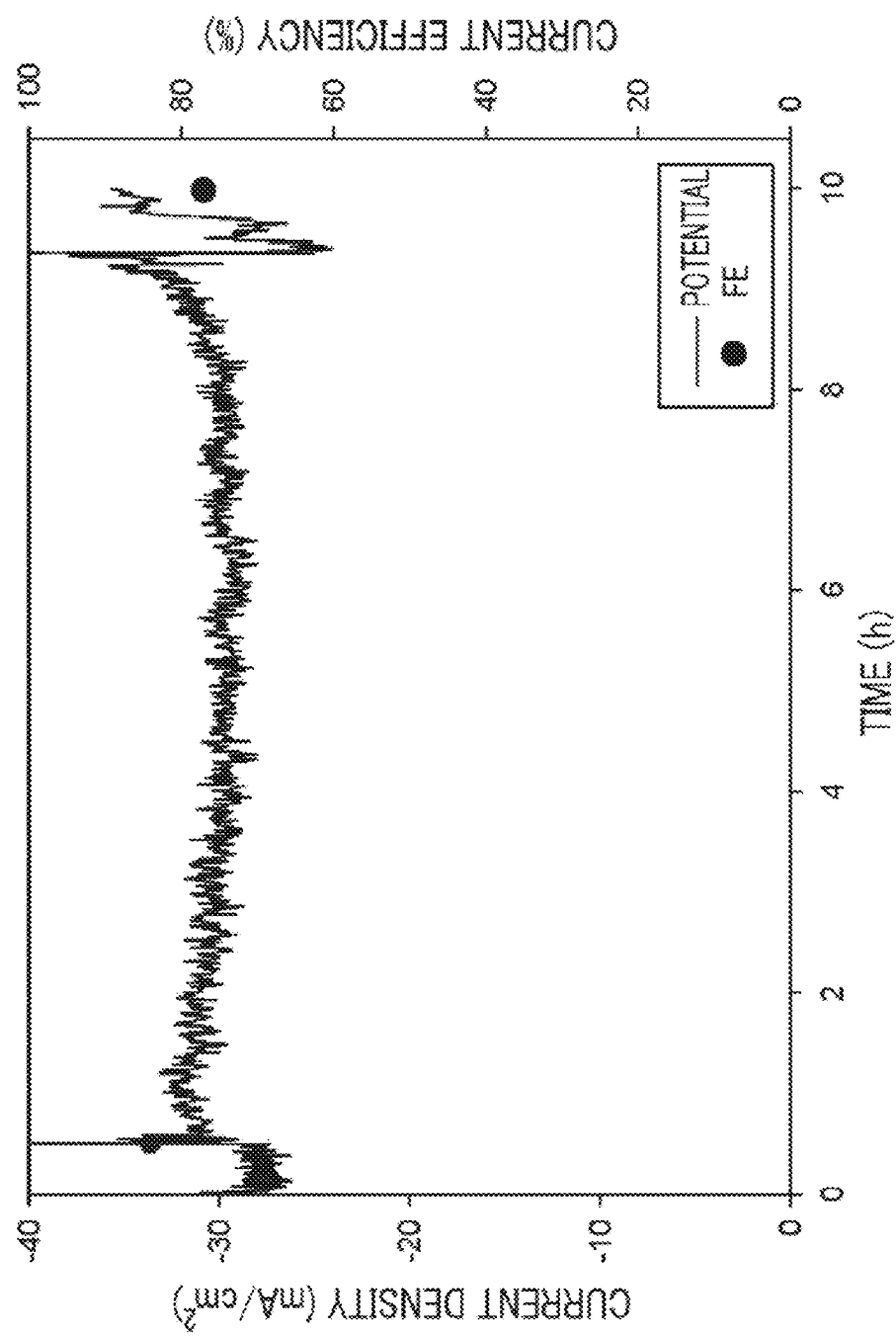
FIG. 11 shows electrolysis of $CO_2$ by an amalgam-coated foam-type copper electrode in a H-type cell including 0.5 M $KHCO_3$ and 2 M KCl in accordance with an example of the present disclosure.

As a result of electrolysis using a rod-type amalgam electrode containing 45% mercury, 24% tin, 17% silver, and 14% copper at a current density of 10 mA·cm$^{-2}$, it was observed that the efficiency of 70% or more was maintained for 10 hours or more with a constant voltage of about −1.9 V (vs. Ag/AgCl). Thus, it was confirmed that the amalgam electrode can make it possible to stably perform electrolysis (FIG. 10), and as a result of electrolysis using an amalgam-coated foam-type electrode at a constant voltage of about −1.9 V, it was observed that the efficiency of about 80% or more was maintained for 10 hours or more (FIG. 11). It was confirmed that the amalgam-coated foam-type electrode can make it possible to perform electrolysis at a current density of 30 mA·cm$^{-2}$ higher than the current density for the rod-type amalgam electrode.

Figure 12:
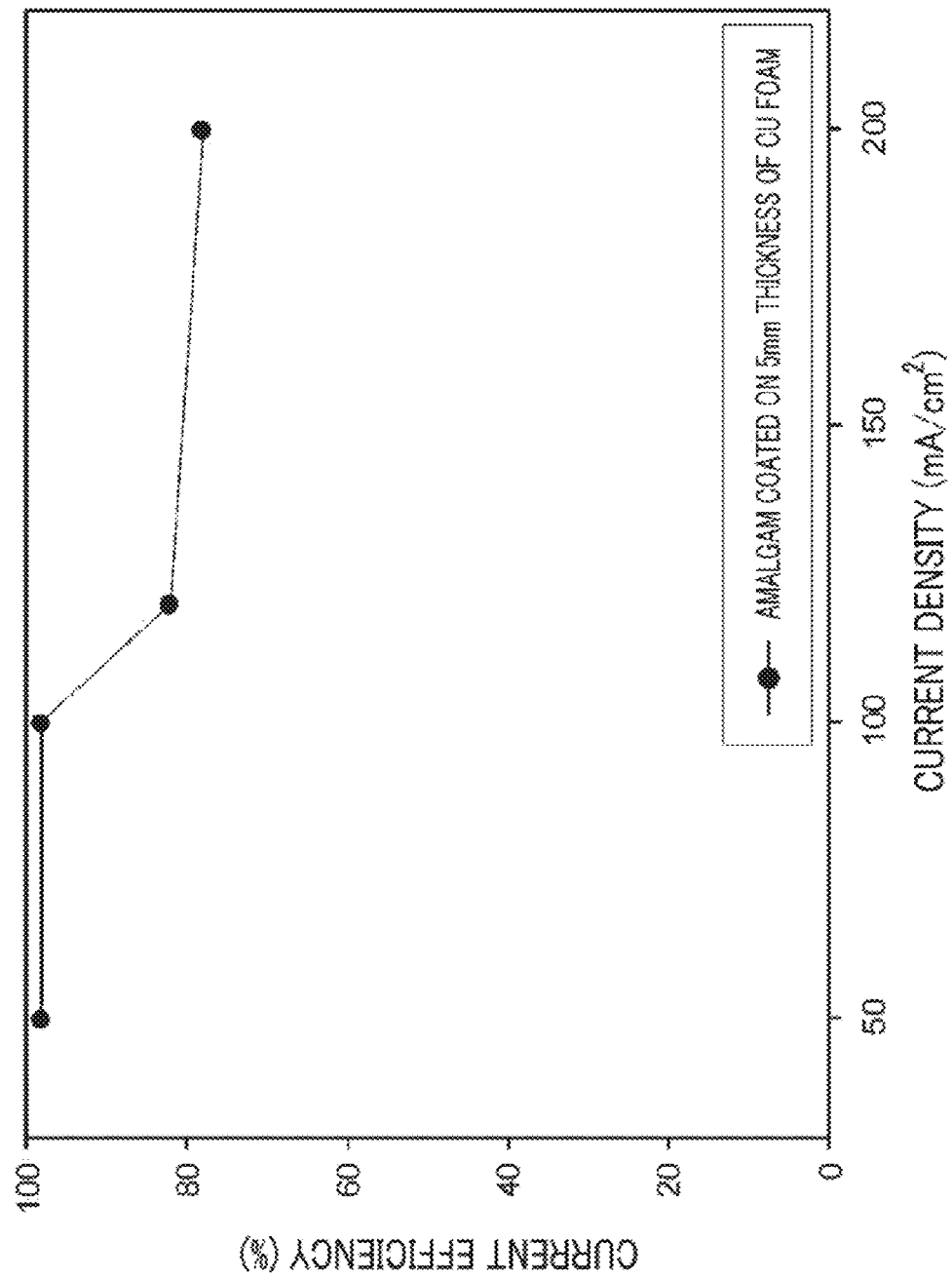
FIG. 12 is a graph showing current density vs. faradaic efficiency of a foam-type amalgam electrode having a thickness of 5 mm during $CO_2$ conversion in accordance with an example of the present disclosure.
Figure 13:
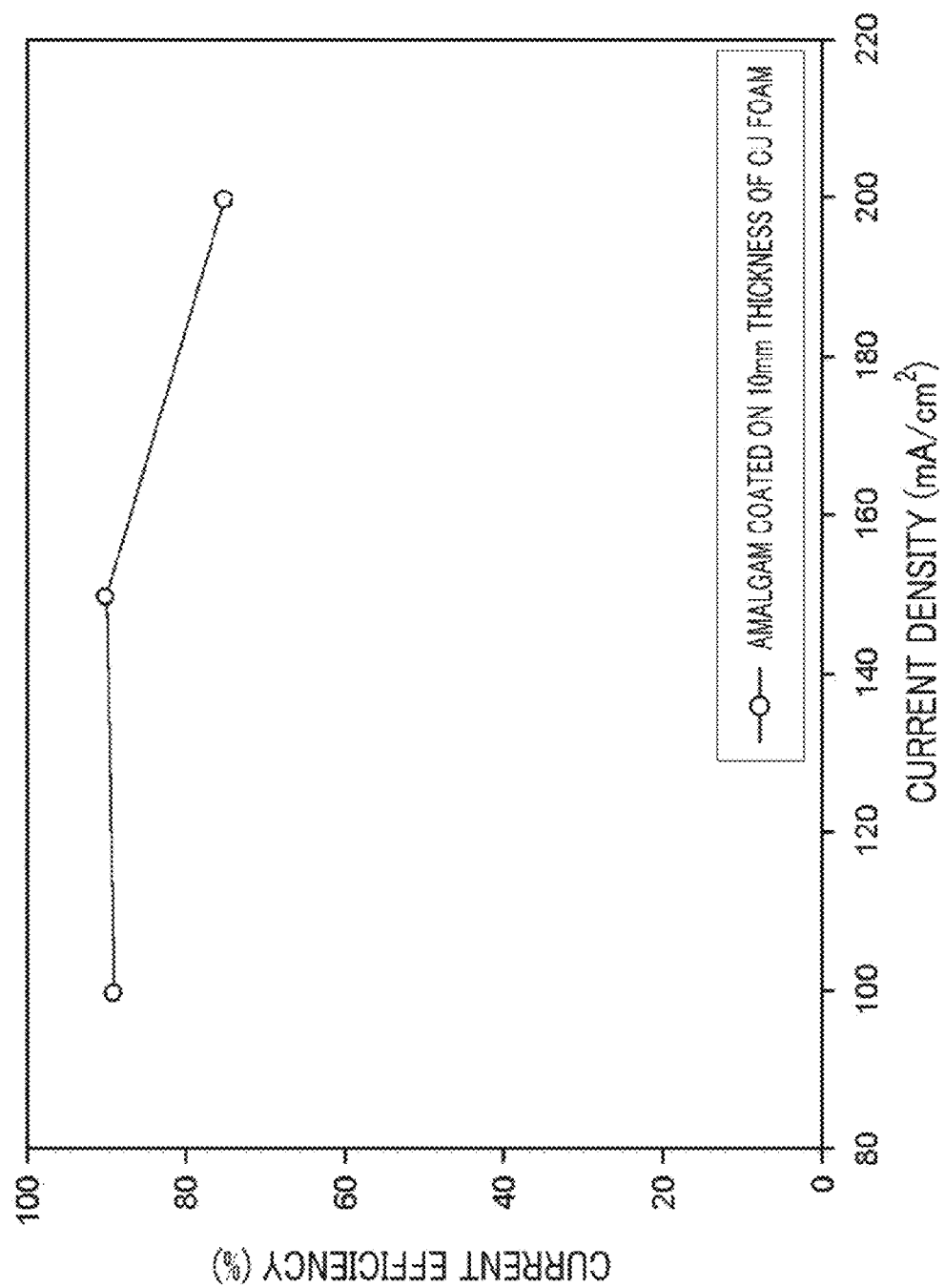
FIG. 13 is a graph showing current density vs. faradaic efficiency of a foam-type amalgam electrode having a thickness of 10 mm during $CO_2$ conversion in accordance with an example of the present disclosure.
Figure 14:
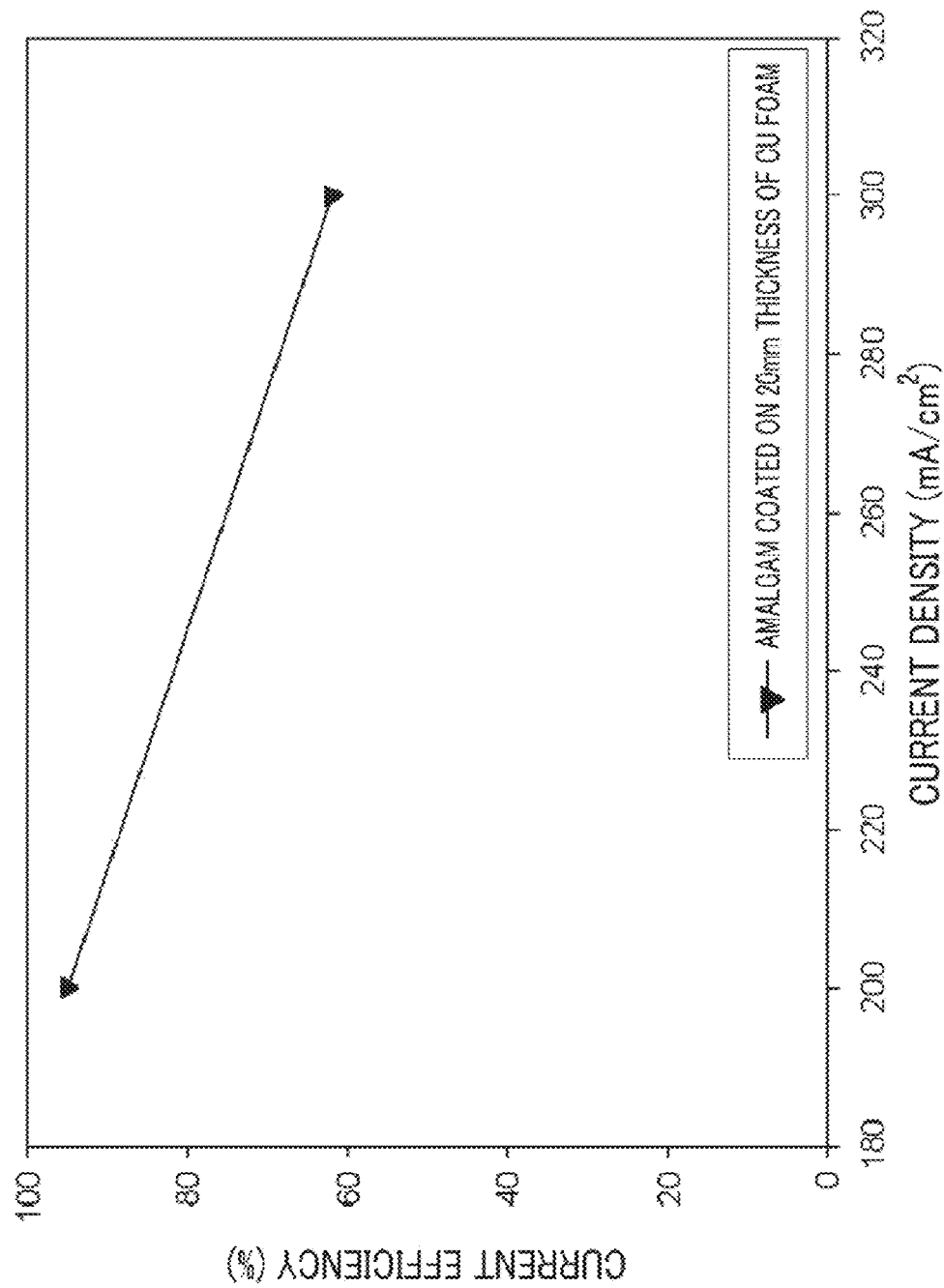
FIG. 14 is a graph showing current density vs. faradaic efficiency of a foam-type amalgam electrode having a thickness of 20 mm during $CO_2$ conversion in accordance with an example of the present disclosure.
Figure 15:
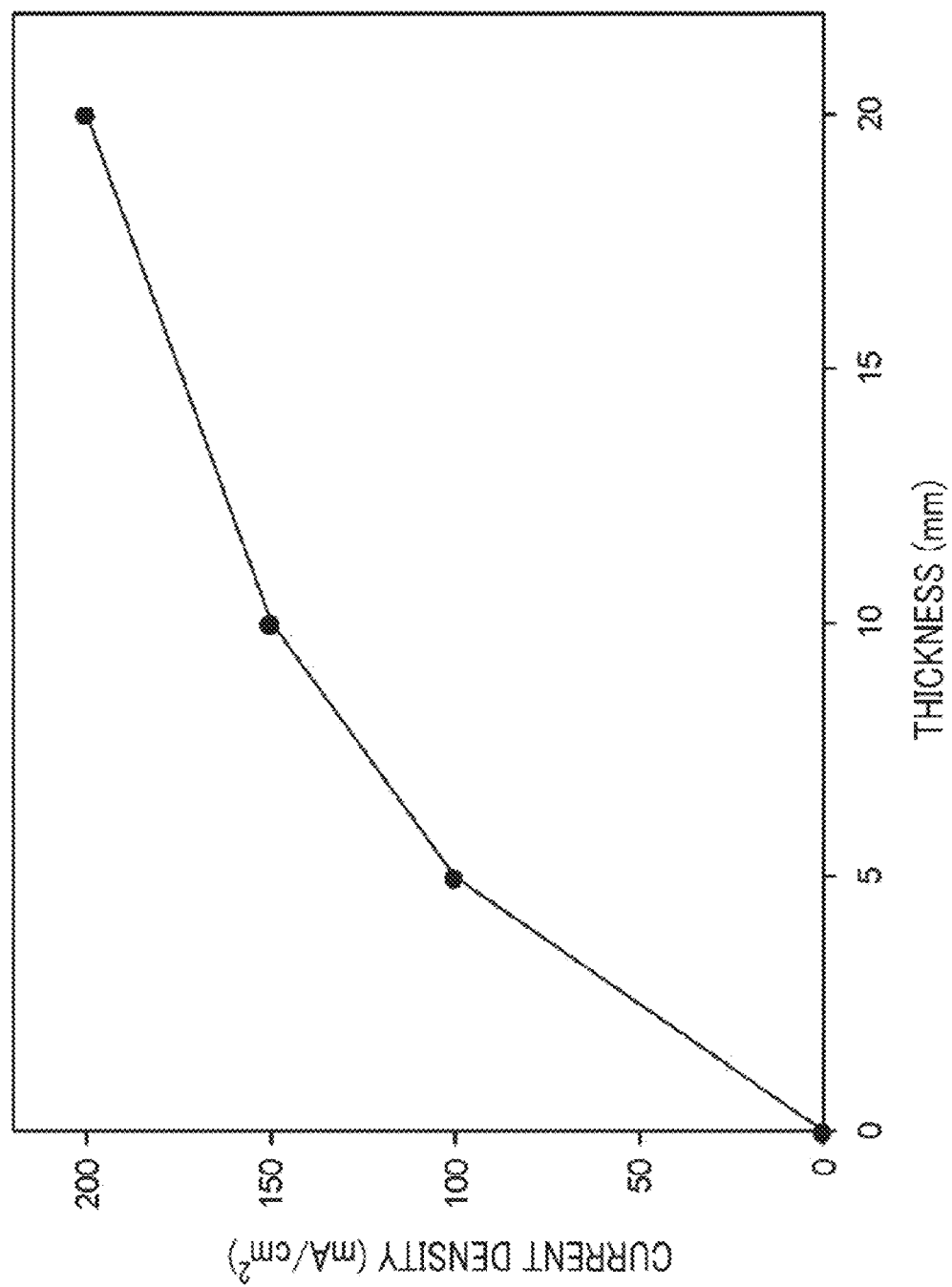
FIG. 15 shows a thickness effect depending on a current density of a foam-type amalgam electrode during $CO_2$ conversion in accordance with an example of the present disclosure.

As a method for increasing a current density, a thickness of the amalgam-coated foam-type electrode having the same apparent area was increased, and then whether or not the current density can be increased was checked. As a result of the test, it was observed that the current efficiency was decreased in an amalgam electrode coated on a foam-type substrate electrode having a thickness of 5 mm at a current density of 100 mA·cm$^{-2}$ or more (FIG. 12), in an amalgam electrode coated on a foam-type substrate electrode having a thickness of 10 mm at a current density of 150 mA·cm$^{-2}$ or more (FIG. 13), and in an amalgam electrode coated on a foam-type substrate electrode having a thickness of 20 mm at a current density of 200 mA·cm$^{-2}$ or more (FIG. 14). A current density before the rapid decrease in efficiency was defined as "limiting current density". As a result of the test, it was confirmed that the current density can be increased by increasing the electrode thickness, but it was observed that the current density vs. thickness was not linearly increased but the increase rate thereof tended to gradually decrease. Thus, it was confirmed that there is a limit in increasing the current density just by increasing the thickness (FIG. 15).

Figure 16:
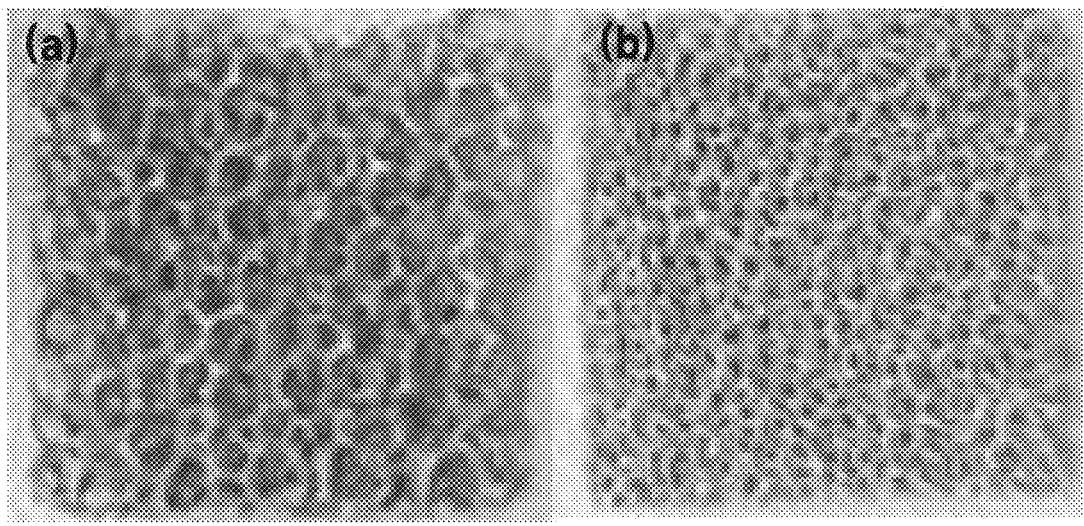
FIG. 16 provides an image of an amalgam-coated 20 ppi foam-type copper electrode (a) and an image of an amalgam-coated 30 ppi foam-type copper electrode (b) in accordance with an example of the present disclosure.
Figure 17:
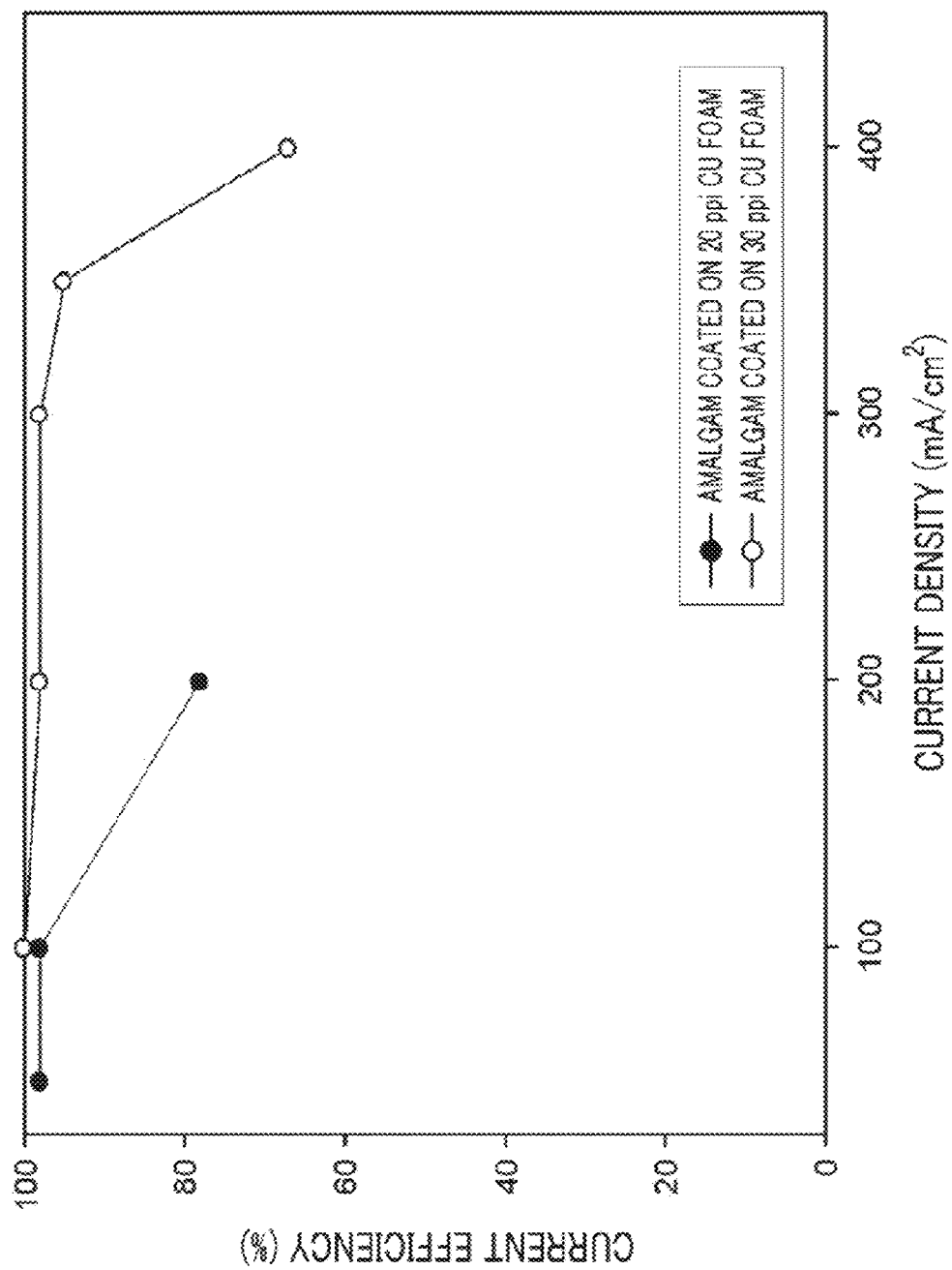
FIG. 17 shows porosity depending on a current density of a foam-type amalgam electrode during $CO_2$ conversion in accordance with an example of the present disclosure.

As another method for increasing a current density, porosity of the amalgam-coated foam-type electrode having the same thickness and the same apparent area was increased to increase an actual surface area, and then whether or not the current density can be increased was checked. As a result of the test, it was observed that in a conventional 20 ppi (pores per inch) electrode [FIG. 16(a)], when the current density was increased by 100 mA·cm$^{-2}$ or more, the efficiency was decreased, whereas in a 30 ppi electrode [FIG. 16(b)], when the current density was increased by 350 mA·cm$^{-2}$ or more, the efficiency was decreased (FIG. 17). Thus, it was confirmed that the surface became dense along with an increase in porosity, so that for the same apparent area, a limiting current density of the electrode can be increased by increasing the actual surface area.

Test Example 2

Obtaining of High-Concentration Formate Salt

Electrochemical reduction of carbon dioxide was performed using the test method and device suggested in the present Example. Further, the effect of maintaining a pH of the anode unit by continuously adding potassium hydroxide (KOH) to the anode unit and the generation of high-concentration of formate salt in the cathode unit were checked.

Figure 18A:
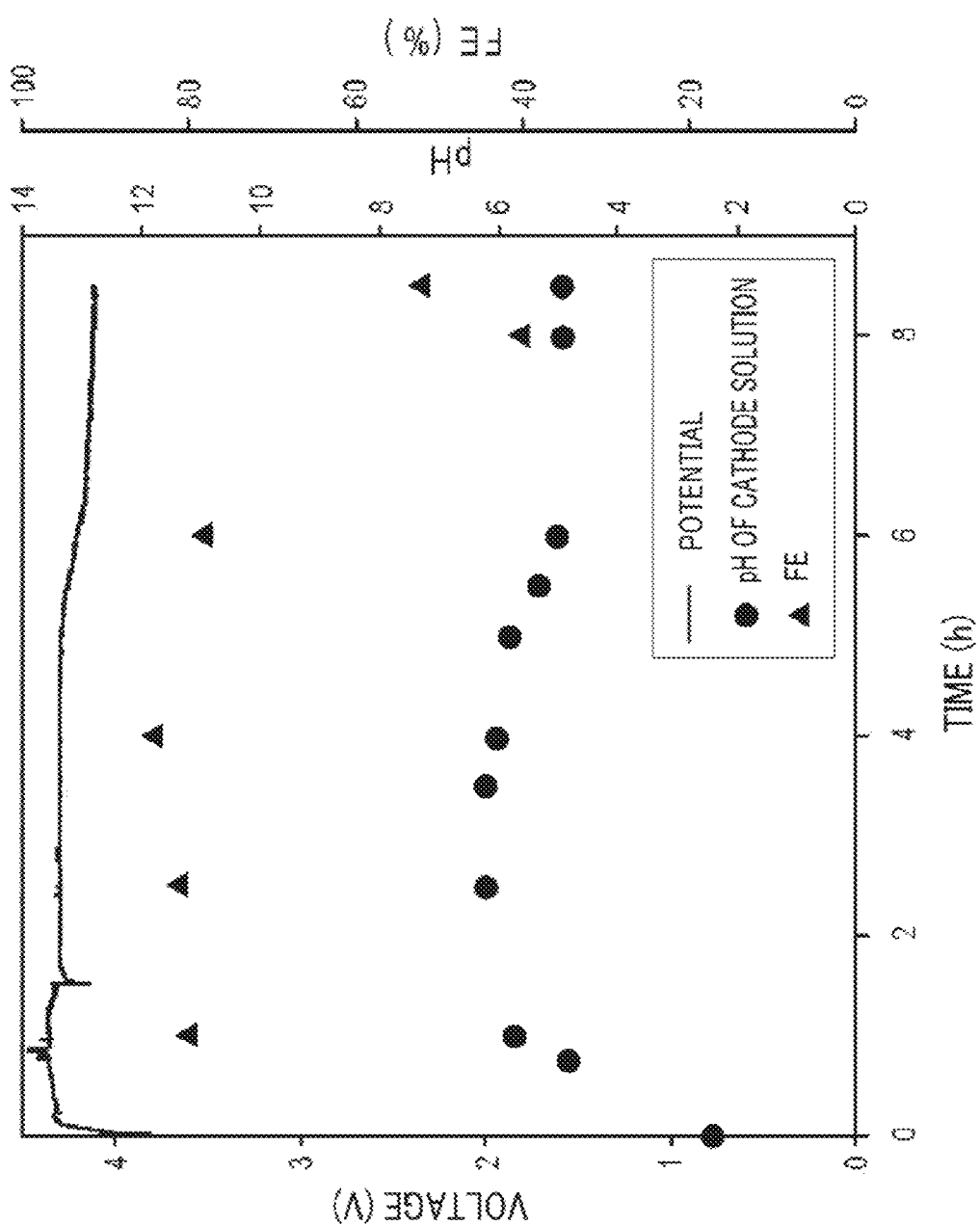
FIG. 18A and FIG. 18B show electrolysis of $CO_2$ by coated amalgam including (FIG. 18A) or without FIG. 18B) a pH feedback system in accordance with an example of the present disclosure.
Figure 18B:
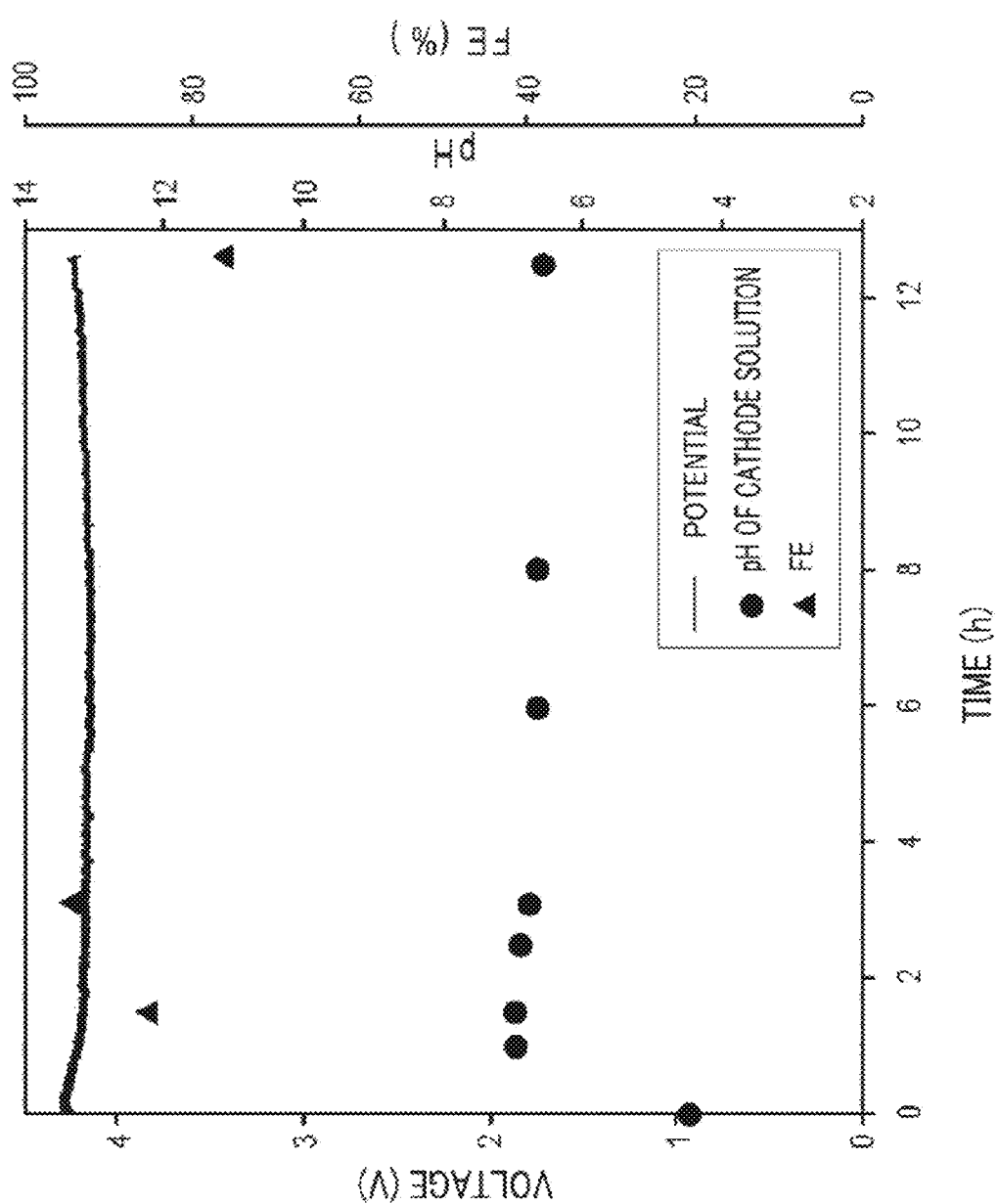

As a result of the test, when KOH was not continuously added to the anode unit under the same conditions, voltage and a pH were rapidly changed 5 hours later and the efficiency of conversion into formate in the cathode unit was decreased down to about 40% 8 hours later (FIG. 18A), whereas when KOH was continuously added to the anode unit, voltage and a pH were uniformly maintained even after electrolysis for 10 hours or more and the efficiency of conversion into formate in the cathode unit was not decreased but stably maintained (FIG. 18B).

Figure 19:
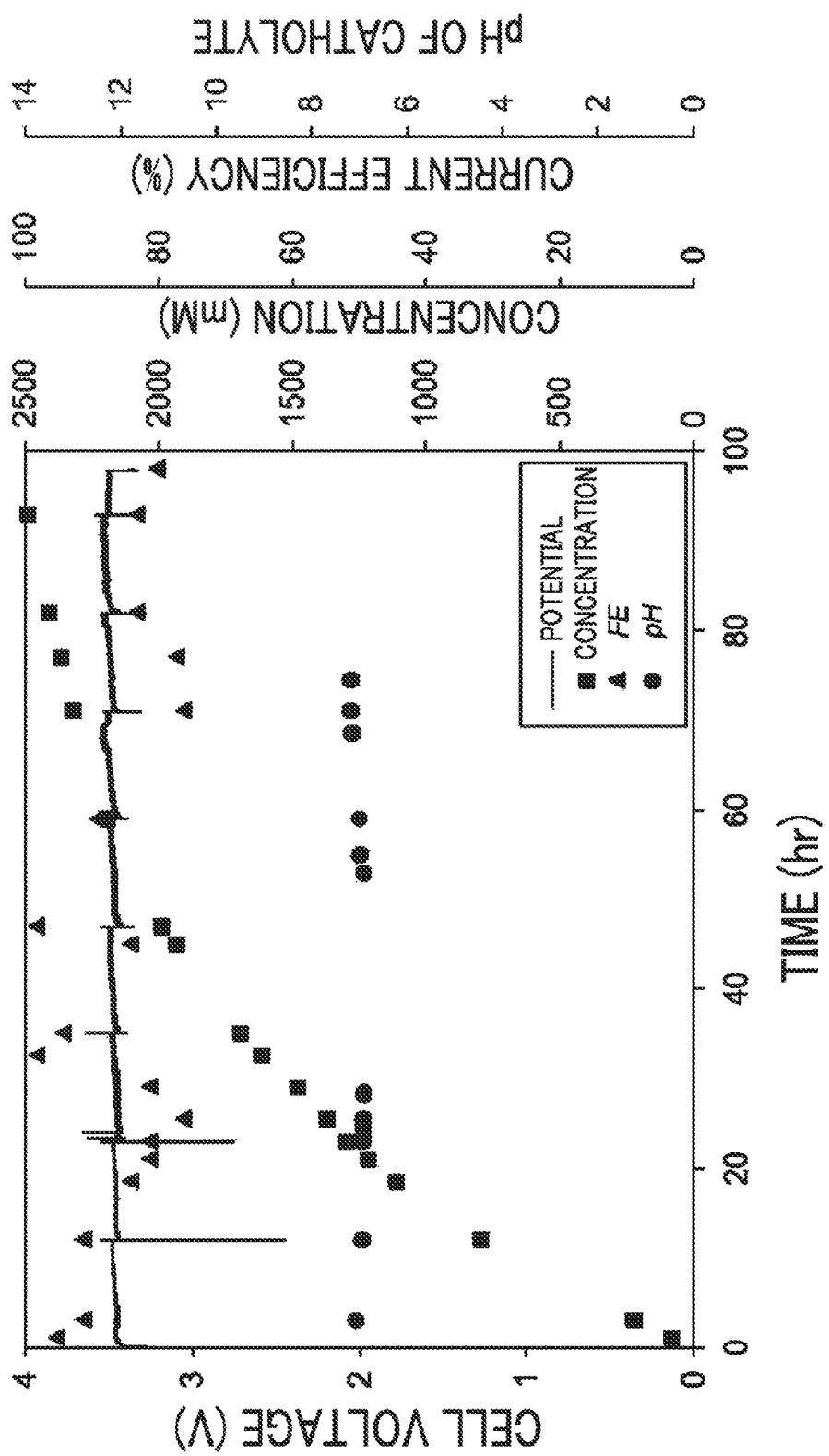
FIG. 19 shows long term electrolysis of $CO_2$ in accordance with an example of the present disclosure.

FIG. 19 is a graph obtained by performing long term electrolysis while continuously adding KOH to the anode unit in accordance with the present Example. It was confirmed that if electrolysis is performed for 60 hours or more while continuously supplying KOH to the anode unit, a pH and potential are stably maintained and more than 2 M formate salt is generated in the cathode unit at a current efficiency of 80% or more. If electrolysis is performed for a longer time, the current density can be maintained at 80% or more until the formate salt has a concentration of about 2.5 M.

The above description of the present disclosure is provided for the purpose of illustration, and it would be understood by those skilled in the art that various changes and modifications may be made without changing technical conception and essential features of the present disclosure. Thus, it is clear that the above-described examples are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

EXPLANATION OF REFERENCE NUMERALS

100: Cathode unit
200: Anode unit
300: Membrane
400: First chamber
410: First pump
500: Second chamber
510: Second pump
600: Supply unit
700: Carbon dioxide supply unit

We claim:

1. A method for electrochemical reduction of carbon dioxide, comprising:
    in a reactor of electrochemical reduction of carbon dioxide including an anode unit and a cathode unit,
    continuously supplying carbon dioxide to the cathode unit and continuously supplying a metal hydroxide to the anode unit; and
    applying voltage and current to the cathode unit and the anode unit for reducing the carbon dioxide to obtain a formate salt,
    wherein the cathode unit includes both Hg and a metal formed on a surface of a foam substrate electrode, and
    wherein the metal includes a member selected from the group consisting of Ag, In, Sn, Pb, Cu, and combinations thereof,
    wherein the metal hydroxide is an alkali metal hydroxide including a member selected from the group consisting of KOH, NaOH, LiOH, and combinations thereof,
    wherein a current density depending on the voltage applied to the cathode unit and the anode unit is between 100 mA/cm$^2$ to 350 mA/cm$^2$, and
    wherein the metal hydroxide is continuously supplied to the anode unit so that a concentration of the formate salt of 1.0 M or more is continuously obtained by reduction of the carbon dioxide.

* * * * *